United States Patent
Kenney et al.

(10) Patent No.: US 8,458,610 B2
(45) Date of Patent: Jun. 4, 2013

(54) MEDICAL INFORMATION GENERATION AND RECORDATION METHODS AND APPARATUS

(75) Inventors: Howard M. Kenney, Spokane, WA (US); Jeffrey B. Butler, Spokane, WA (US); Gary L. Craig, Colbert, WA (US); Sean P. LaSalle, Spokane, WA (US); Eric C. Mueller, Spokane, WA (US); Karen M. Ferguson, Colbert, WA (US)

(73) Assignee: Discus Investments, LLC, Spokane, WA (US)

(*) Notice: Subject to any disclaimer, the term of this patent is extended or adjusted under 35 U.S.C. 154(b) by 189 days.

(21) Appl. No.: 12/726,281

(22) Filed: Mar. 17, 2010

(65) Prior Publication Data

US 2011/0231786 A1    Sep. 22, 2011

(51) Int. Cl.
G06F 3/00         (2006.01)
G06F 3/048        (2006.01)

(52) U.S. Cl.
USPC .......................................... 715/771; 715/705

(58) Field of Classification Search
USPC ......................................... 715/771, 705, 769
See application file for complete search history.

(56) References Cited

U.S. PATENT DOCUMENTS

| | | | |
|---|---|---|---|
| 8,265,955 B2 | 9/2012 | Michelson et al. | |
| 2004/0009459 A1 | 1/2004 | Anderson et al. | |
| 2004/0193019 A1 | 9/2004 | Wei | |
| 2006/0031094 A1 | 2/2006 | Cohen et al. | |
| 2006/0061574 A1* | 3/2006 | Ng-Thow-Hing et al. | 345/473 |
| 2006/0111933 A1 | 5/2006 | Wheeler | |
| 2006/0241977 A1 | 10/2006 | Fitzgerald et al. | |
| 2008/0077446 A1 | 3/2008 | Korpman et al. | |
| 2008/0270183 A1 | 10/2008 | Hawkins et al. | |
| 2009/0076371 A1* | 3/2009 | Lang et al. | 600/407 |
| 2009/0131758 A1* | 5/2009 | Heywood et al. | 600/300 |
| 2009/0192823 A1 | 7/2009 | Hawkins et al. | |
| 2009/0318775 A1 | 12/2009 | Michelson et al. | |
| 2010/0256479 A1* | 10/2010 | Park et al. | 600/410 |
| 2012/0016233 A1* | 1/2012 | Kalafut et al. | 600/432 |
| 2012/0053425 A1 | 3/2012 | Michelson et al. | |
| 2012/0116223 A1* | 5/2012 | Da Silva et al. | 600/442 |

FOREIGN PATENT DOCUMENTS

| | | |
|---|---|---|
| KR | 10-2011-0003352 | 1/2011 |
| WO | WO 2007-059477 | 5/2007 |
| WO | PCT/US2011/028112 | 9/2011 |
| WO | PCT/US2011/028112 | 9/2012 |
| WO | PCT/US2012/054285 | 2/2013 |

OTHER PUBLICATIONS

DAS28—Disease Activity Score in 28 Joints (DAS28); www.iche.edu/newsletter/DAS28.pdf; Feb. 5, 2009; 2 pp.
Enbrel etanercept Stamp; 2007; 9 pp.

* cited by examiner

*Primary Examiner* — Weilun Lo
*Assistant Examiner* — Truc Chuong
(74) *Attorney, Agent, or Firm* — Wells St. John P.S.

(57) ABSTRACT

Computer-implemented medical information recording methods are described. According to one aspect, a computer-implemented medical information recording method includes displaying a graphical user interface including a graphical representation of the human anatomy, accessing user inputs interacting with the graphical representation of the human anatomy, and generating an electronic record comprising data pertaining to the health of the patient using the user inputs interacting with the graphical representation of the human anatomy.

24 Claims, 9 Drawing Sheets

_Fig. 1_

_Fig. 2_

| Joint | Tender | Swl | ROM | Def | Repl |
|---|---|---|---|---|---|
| Left Elbow | X | | | | |
| Left GHJ | | X | | | |
| Left IP | | X | | | |
| Left knee | X | | X | | |
| Left MCP I | X | | X | X | |
| Left MCP II | X | | | | |
| Left MCP III | X | | X | | |
| Left MCP IV | X | | X | | |
| Left MCP V | X | | | X | |
| Left PIP II | | | | | |

Set Condition
- ☐ Normal
- ☒ Tender
- ☐ Swelling
- ☐ ROM Dec
- ☐ Deformity
- ☐ Replaced

Display
- ○ Normal   ○ Deformity
- ○ Tender   ○ Replaced
- ○ Swelling ● All
- ○ ROM Dec  ○ Hold

Include in Chart Note:
- ☒ Joint count totals
- ☐ Joint count table
- ☐ DAS28

☐ All joints are normal.
☐ All REMAINING joints are normal.

Today's Totals / Last Visit
- Tender: 10 / 5
- Swelling: 13 / 10
- Dec ROM: 3 / 0
- Deformity: 2 / 2

% change [   ][   ][   ][   ]

Update    Chart

DAS28
- ☐ Load JC Data
- Swollen (0-28): 13
- Tender (0-28): 10
- ESR (mm/hr): [   ]   ☐ Task lab
- VAS GH: [   ]   VAS
- DAS28: 1.12
- DAS28 (prior): 1.25
- % Change: [   ]

Calculate Totals

○ ○ ○

HAQ
- Activity
- Tender
- Anxiety
- Patient GH
- HAQ

DAS28 Trend

Save & Close

PQRI - RA

FIG. 3

PQRI for RA

This visit qualifies for PQRI submission: ☐

Code Submission: ○ On ◉ Off    [Auto-Eval 1-4]   [Refresh]    [Save & Close]

1. RA Functional Status Assessment — HAQ was performed at least once in the last 12 months ☐ #178
- ○ HAQ performed
- ○ HAQ NOT performed for reason specified Last HAQ & Date: [4:00] [03/25/2009] HAQ

2. DMARD

☐ #108
- ○ Patient on DMARD or prescribed DMARD today
- ○ Not prescribed / administered DMARD for documented medical reasons
- ○ Not prescribed / administered for reason not specified Pt Currently Receiving: [DOXYCYLINE]

3. TB Screen — Patient prescribed first time biologic DMARD for RA AND:

☐ #176
- ○ TB screen performed w/in 6 months prior to 1st time biologic DMARD therapy
- ○ TB screen NOT performed for documented medical reasons
- ○ TB screen NOT performed for reason not specified OR
- ○ Does not apply because biologic DMARD is Rituximab or this is not the 1st course of biologic DMARD for RA Last TB Result & Date: [ ] [ / / ]   Pt not taking bio. DMARD

4. Periodic Assessment of Disease Activity — Patient has had a DAS28 completed w/in last 12 months ☐ #177
- Disease activity:  ○ Low   ○ Moderate   ○ High OR
- ○ Disease activity not assessed and classified for reason not specified Last DAS28 & Date: [1.12] [03/11/2010]

5. RA Assessment and Classification of Disease Prognosis

☐ #179  Classification of disease prognosis has been documented in the last 12 months based upon:
- HAQ
- Extraarticular disease
- RF +, Anti-CCP +
- Radiographic erosions ○ POOR prognosis documented
  ○ GOOD prognosis documented
  ○ Disease prognosis NOT assessed and classified for reason not specified

6. RA Glucocorticoid Management

☐ #180  Patient diagnosed with RA and has been assessed for glucocorticoid use and, for those on prolonged doses of prednisone > 10mg daily (or equivalent) with improvement or no change in disease activity, glucocorticoid management plan has been documented in the last 12 months ○ Patient NOT receiving glucocorticoid therapy
  ○ Patient on < 10mg daily prednisone, -or- RA disease activity is worsening, -or- glucocorticoid use is for < 6 months
  ○ Patient on > 10mg daily prednisone (or equivalent) > 6 months, and improvement or no change in disease activity, and glucocorticoid management plan HAS been documented
  ○ Same as above, but the management plan is NOT documented for MEDICAL REASONS
  ○ Same as above, but the management plan is NOT documented for REASON NOT SPECIFIED
  ○ Glucocortocoid DOSE not documented for reason not specified Changes Submitted This Encounter

| Description | CPT | Mod |
|---|---|---|
|  |  |  |
|  |  |  |

Save & Close

FIG. 6B

| DATE OF SERVICE: | Thursday, March 11, 2010 |
| PATIENT NAME: | Karen Test |
| DATE OF BIRTH: | 04/24/1953 |
| MRN: | |
| PROVIDER: | |

CURRENT MEDICATIONS:

| Medication | Dose | Sig Description |
|---|---|---|
| Doxycycline | 150mg | Take one tablet by mouth two times per day |
| Hydroxychloroquine Sulfate | 200mg | Take 1 tablet (200MG) by ORAL route every day |
| Enbrel Sure Click Injector | 50mg | 1 ml sub Q weekly |
| Enbrel Sure Click Injector | 50mg | 2.0 ml subcutaneously Q week |
| Foscarnet Sodium | 24mg/ml | |
| Aspirin | 81 Mg | 2 |
| Aspirin | 81 Mg | 1-2 tabs po Q 4-6 hours pm pain |

ALLERGIES:

| Description | Reaction |
|---|---|
| Pseudoephedrine Hcl | |
| Penicillin G Potassium | |
| Diphenhydramine Hcl | |
| Diphenhydramine | |
| Acetaminophen | |

PATIENT HISTORY:
Past Medical History:
The patient has had the following problems or illnesses:

| Problem/Illness | Comments |
|---|---|
| Cataracts | |
| Anemia | |

PHYSICAL EXAM:
Joint Count:

| Joint Name | Tender | Swelling | Rom | Deformity | Replaced |
|---|---|---|---|---|---|
| Left AC | X | | | | |
| Left Ankle | | X | | | |
| Left CMC | X | X | | | |
| Left DIP II | | | X | | |
| Left DIP II toe | | | | | X |
| Left DIP III | X | | | | |

| | | | | |
|---|---|---|---|---|
| Left DIP III toe | X | | X | |
| Left DIP IV | | | | X |
| Right MCP II | | X | | |
| Right MCP III | X | X | | |
| *** | *** | | | |
| *** | *** | | | |
| *** | *** | | | |
| Right TMJ | | | | X |
| Right Wrist | | | X | |

DAS28:

The Disease Activity Score, including a 28-joint count, was calculated for the patient. The results are as follows:

Number of swollen joints: 13
Number of tender joints: 10
ESR (mm/hr):
VAS General Health:

DAS28:   1.12
Prior DAS28:   1.25

Document generated by Joe Smith at 03/11/2010 1:09 PM.

MEDICAL INFORMATION GENERATION AND RECORDATION METHODS AND APPARATUS

TECHNICAL FIELD

This disclosure relates to medical information generation and recordation methods and apparatus.

BACKGROUND OF THE DISCLOSURE

The use of computing devices is ubiquitous in the workplace to implement numerous tasks in numerous different applications. For example, in the medical field, physician notes regarding patients were traditionally kept in a series of papers within a chart. The treating physician could review the patient's chart before examining the patient to gain information regarding the patient's previous health history. In addition, the physician may add new notes resulting from a recent examination. These charts may be stored electronically for ease of use, management, and recollection.

At least some aspects of the disclosure are directed to methods and apparatus for generating and recording medical information pertinent to a patient's health. In some aspects, the medical information may be efficiently used by medical personnel for treatment of the patient. Other aspects are disclosed as is apparent from the following detailed description.

BRIEF DESCRIPTION OF THE DRAWINGS

Exemplary embodiments of the disclosure are described below with reference to the following accompanying drawings.

FIG. 3 is a graphical user interface used by medical personnel to input and review information regarding a patient's health according to one embodiment.

FIG. 6 is a map illustrating how FIGS. 6A and 6B are to be assembled. Once assembled, FIGS. 6A and 6B are an example template which may be used to provide information to a medical agency according to one embodiment.

FIG. 7 is a map illustrating how FIGS. 7A and 7B are to be assembled. Once assembled, FIGS. 7A and 7B are an example chart note of the patient's examination according to one embodiment.

DETAILED DESCRIPTION OF THE DISCLOSURE

This disclosure is submitted in furtherance of the constitutional purposes of the U.S. Patent Laws "to promote the progress of science and useful arts" (Article 1, Section 8).

At least some aspects of the disclosure are directed to methods, apparatus and programming to assist physicians and other medical personnel with generating and recording of data pertaining to the health of patients. In one embodiment, the generation of a plurality of different reports is facilitated. Trends of information regarding a patient's health may be tracked over time and charted in another embodiment. A graphical user interface corresponding to the human anatomy is provided in one embodiment to facilitate inputting and recording of information regarding a patient, such as information relating to joints. In another embodiment, data regarding the patient's health may be used to generate a value for an outcome measure which is indicative of a level of disease activity in a patient, and which may be used in some embodiments to evaluate past treatment and to determine appropriate treatment for the patient in the future. Other aspects and embodiments are described below.

According to one embodiment, a computer-implemented medical information recording method comprises displaying a graphical user interface including a graphical representation of the human anatomy, accessing user inputs interacting with the graphical representation of the human anatomy, and generating an electronic record comprising data pertaining to the health of the patient using the user inputs interacting with the graphical representation of the human anatomy.

According to an additional embodiment, computer-implemented method for generating medical information for a patient comprises displaying a graphical user interface having a graphical representation of a plurality of different joints of the human anatomy; accessing user inputs which interact with at least some of the joints of the graphical representation of the human anatomy; as a result of the user inputs, associating a plurality of different conditions with different ones of the joints for a patient; and using the joints with the associated conditions, determining a value of an outcome measure which is indicative of a level of activity of arthritis in the patient.

According to yet another embodiment, an article of manufacture comprises at least one computer-readable media comprising programming configured to cause processing circuitry to perform processing comprising: displaying a graphical user interface including a graphical representation of the human anatomy, wherein the graphical representation includes a plurality of joints; accessing user inputs interacting with the graphical representation of the human anatomy; as a result of the user inputs, associating a plurality of different conditions with different joints of a patient; and displaying information regarding the different conditions associated with the different joints of the patient.

Figure 1:
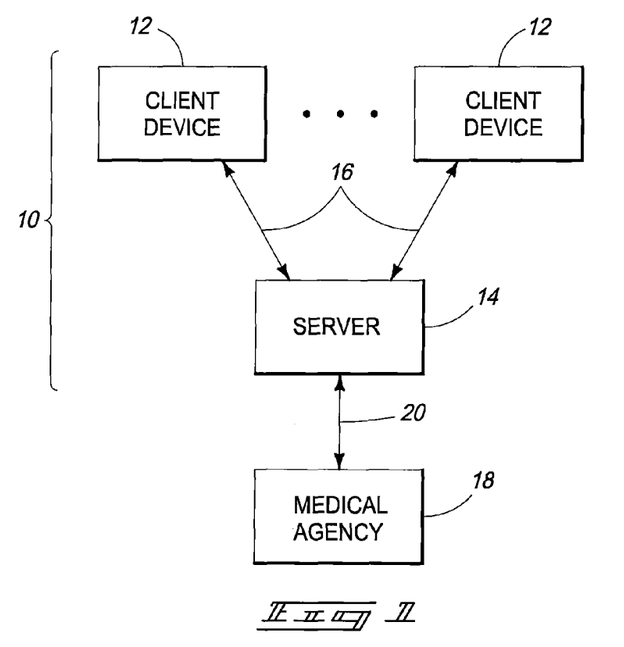
FIG. 1 is a functional block diagram of a computing system according to one embodiment.

Referring to FIG. 1, a computing system 10 which is configured to implement some aspects of the disclosure is shown according to one example embodiment. The illustrated computing system 10 includes one or more client devices 12, a server 14 and a communications media 16 configured to implement communications intermediate client devices 12 and server 14. The computing system 10 may be implemented within a physician's office and be secured in one embodiment.

Server 16 is configured to additionally communicate with other devices or systems which may be external of the computing system 10 (e.g., a medical agency 18 described below) via a communications media 20. Server 14 may communicate via communications media 20 with the external devices. Communications media 20 may be the Internet in one example implementation. Other configurations of computing system 10 are possible. For example, server 14 may be omitted in some arrangements and aspects of the disclosure may be implemented using a client device 12.

Client devices 12 may be configured as personal or portable notebook computers in example implementations. Medical personnel (e.g., physicians, physician assistants, nurses, etc.) may communicate with patients during examinations and use the client devices 12 to input, generate and record information pertaining to the health of the patients. The inputted information may result from patient's answers to diagnosis questions and/or results of examinations and tests in some examples Client devices 12 may communicate the information to server 14 via communications media 16 which may be implemented as a local area network in one example (e.g., utilized within a physician's office). The information regarding the health of the patients may be provided into an electronic record corresponding to the patient and communicated to server 14 for storage, for example within a database. The electronic records may be reviewed at later moments in time and supplemented with additional information as the patient is treated by the medical personnel.

Server 14 may include a database configured to store the electronic records including information regarding the patient's health for later retrieval. Furthermore, server 14 may use the information regarding a patient's health to generate additional information regarding the patient's health. The generated information may include charts, graphs, outcome measures and other information regarding the patient and which may also be provided within the electronic record of the patient. In some embodiments, individual client devices 12 may generate additional information regarding the patient's health and include the data within an electronic record for the patient which is communicated to the server 14.

Figure 2:
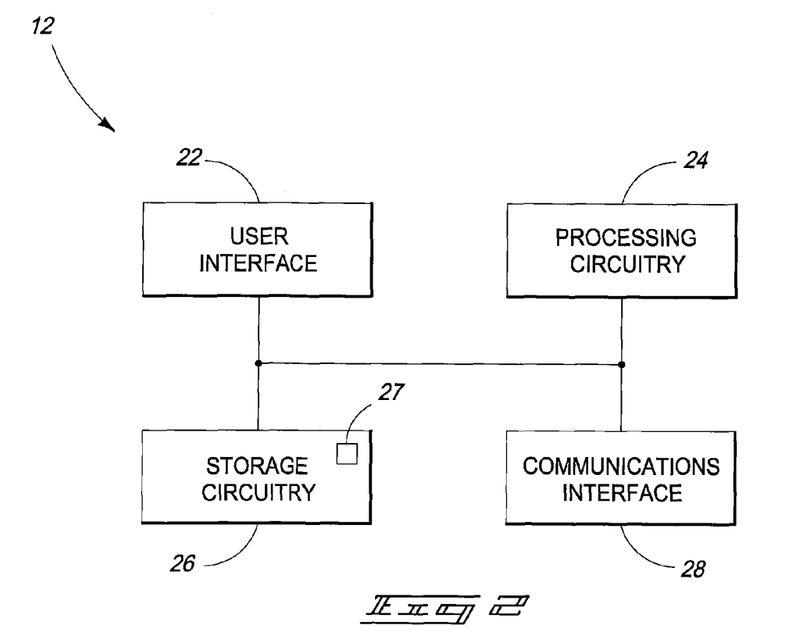
FIG. 2 is a functional block diagram of a client device according to one embodiment.

Referring to FIG. 2, details of one example embodiment of a client device 12 in the form of a personal or notebook computer is shown. In the depicted example, the client device 10 includes a user interface 22, processing circuitry 24, storage circuitry 26 and a communications interface 28. Other configurations of client device 10 are possible including more, less and/or alternative components. Although not described in detail, server 14 may also be configured to include the components depicted in FIG. 2 in one example embodiment.

User interface 22 is configured to interact with a user including conveying data to a user (e.g., displaying visual images for observation by the user) as well as receiving inputs from the user, for example via a keyboard and point device (e.g., mouse). User interface 22 is configured as graphical user interface (GUI) in one example embodiment.

In one embodiment, processing circuitry 24 is arranged to process data, control data access and storage, process data to generate reports, issue commands, and control other desired operations. Processing circuitry 24 may comprise circuitry configured to implement desired programming provided by appropriate computer-readable storage media in at least one embodiment. For example, the processing circuitry 24 may be implemented as one or more processor(s) and/or other structure configured to execute executable instructions including, for example, software and/or firmware instructions. Other exemplary embodiments of processing circuitry 24 include hardware logic, PGA, FPGA, ASIC, state machines, and/or other structures alone or in combination with one or more processor(s). These examples of processing circuitry 24 are for illustration and other configurations are possible.

Storage circuitry 26 is configured to store programming such as executable code or instructions (e.g., software and/or firmware), electronic data, databases, image data, electronic reports or other digital information and may include computer-readable storage media. At least some embodiments or aspects described herein may be implemented using programming stored within one or more computer-readable storage medium of storage circuitry 26 and configured to control appropriate processing circuitry 24.

The computer-readable storage medium may be embodied in one or more articles of manufacture 27 which can contain, store, or maintain programming, data and/or digital information for use by or in connection with an instruction execution system including processing circuitry 24 in the exemplary embodiment. For example, exemplary computer-readable storage media may include any one of physical media such as electronic, magnetic, optical, electromagnetic, infrared or semiconductor media. Some more specific examples of computer-readable storage media include, but are not limited to, a portable magnetic computer diskette, such as a floppy diskette, a zip disk, a hard drive, random access memory, read only memory, flash memory, cache memory, and/or other configurations capable of storing programming, data, or other digital information.

Communications interface 28 is arranged to implement communications of client device 12 with respect to external devices (such as server 14). For example, communications interface 28 may be arranged to communicate information bi-directionally with respect to external devices. Communications interface 28 may be implemented as a network interface card (NIC), serial or parallel connection, USB port, Firewire interface, flash memory interface, or any other suitable arrangement for implementing communications with respect to external devices.

As mentioned above, client devices 12 may be used by medical personnel during patient examinations to generate and record information pertinent to the health of the patient. At least some aspects of the disclosure are directed to methods, apparatus and programming which enable medical personnel to efficiently input information ascertained from examinations for recordation, storage, subsequent retrieval, and generation of additional information regarding the patient's health in some examples. Some aspects of the disclosure are directed to facilitating generation of patient reports using the stored information regarding the patients' health. The information regarding the patient's health may be used to develop trend information indicative of the patients' health over time. At least some aspects are directed to generation of the patient reports into formats which may be easily retrievable and utilized by other entities, such as medical agencies 18 discussed above. Furthermore, the information regarding the patient's health may be used to provide an outcome measure which may indicate a level of activity of a disease in a patient and which may indicate how the patient has responded to treatment and may be used to determine appropriate courses of treatment in the future.

Referring to FIG. 3, one embodiment of a graphical user interface 30 which may be displayed by a client device 12 is shown. The example depicted graphical user interface 30 may be used by medical personnel during examination of patients to input information and display previous information regarding previous examinations, for example, including trend data comprising information regarding a patient's health over time. The example embodiment of FIG. 3 is intended to assist rheumatologists in treating patients with rheumatoid arthritis. Other embodiments may be directed to assist other types of medical personnel with other types of medical treatment and may include other graphical user interfaces which include graphical representations of other parts of the human anatomy in some examples.

In the depicted example, the graphical user interface 30 includes a representation 32 of the human anatomy. The graphical representation 32 includes a plurality of selectable portions 34 which correspond to different portions of the human anatomy and which may be selected by user inputs of a user (e.g., medical personnel). For example, the user inputs may be provided by a user using an interactive pointing device (e.g., mouse) resulting from the examination of the patient and which interact with selectable portions 34 of the human anatomy. In the depicted example directed towards treatment of rheumatoid arthritis, the selectable portions 34 correspond to different joints of the human anatomy. In a more specific example discussed below, the user may select one or more joint of the human anatomy and associate one or more condition with the selected joint(s).

The illustrated embodiment of the graphical user interface 30 includes a set condition window 36 which includes a plurality of conditions (e.g., normal, tender, swelling, range of motion limited, deformity, replaced) which correspond to a plurality of different conditions of the human joints. During an examination of the patient, the medical personnel may use representation 32 and window 36 to inventory conditions of the patient's joints. For example, the medical personnel may select the "tender" option of the different conditions, and thereafter select the respective portions (e.g., joints) 34 which the patient indicates are currently tender or are otherwise painful. This may be repeated for the other conditions until each of the joints are labeled with an appropriate condition corresponding to the state of the patient's joints during the examination. Boxes 40, 41 are also provided to assist the medical personnel with quickly indicating that all joints are normal, or all remaining joints are normal in the depicted arrangement.

In one embodiment, data pertaining to the health of the patient resulting from the examination may be displayed in the graphical representation 32. In one embodiment, the different joints of the graphical representation 32 having different conditions may be labeled using different colors which respectively correspond to the different conditions. In one embodiment, the text of the individual conditions of window 36 may also be color coded to the respective colors used to indicate the conditions of the joints in the graphical representation 32. For example, the data of the patient may be displayed by illustrating some joints in the graphical representation 32 as one color (e.g., red) corresponding to a respective condition (e.g., tender) while joints having another condition (e.g., swelling) may be displayed as second color (e.g., purple).

Window 46 illustrates an example of a joint count table which includes a plurality of entries (e.g., textual listing of the joints of the body) and data for the respective entries (e.g., conditions of the respective joints for the patient). In one embodiment, the joint count table is automatically generated by the processing circuitry without further user input once the medical personnel uses the graphical representation 32 to input the conditions of the joints of the patient. Accordingly, in the described example embodiment, the medical personnel may efficiently and accurately input the conditions using the graphical representation 32 which may then be utilized to automatically generate the joint count table which may otherwise have to be created by hand. In addition, the option may exist for the medical personnel to interact directly with joint count table and to input and/or change conditions for respective ones of the joints directly using the joint count table. The generated information (e.g., the graphical representation 32 having the selected conditions/colors, joint count table, etc.) may be recorded and efficiently imported into subsequently generated reports in one embodiment.

The graphical user interface 30 may be utilized by the medical personnel to quickly change the conditions displayed by the graphical representation 32. For example, the medical personnel may select one, some or all of the different conditions to be displayed on the respective joints of the graphical representation 32. More specifically, a display window 38 is provided in the depicted example of FIG. 3 which lists the different conditions which the medical personnel can select to control the conditions which are displayed using the graphical representation 32. For example, the user may select "swelling" to have the joints which were assigned the "swelling" condition highlighted in the graphical representation 32 with the respective color. This permits the medical personnel to quickly change between the respective conditions and easily determine which joints have the respective conditions. In addition, "all" joints may also be selected where all the conditions of all the joints may be displayed in the graphical representation 32.

An additional window 48 is provided in the example of FIG. 3 which lists numerical totals of the joints having the different conditions "tender," "swelling," "decreased range of motion," and "deformity." Following the association of the different conditions with respective ones of the joints using graphical representation 32, the user may select the "update" button of window 48 to have the processing circuitry 14 generate the joint totals for the different conditions and display of the joint totals in window 48 under "today's totals." In other embodiments, the processing circuitry 14 automatically updates the joint total information without additional user interaction as the user assigns the conditions to the respective joints.

Figure 4:
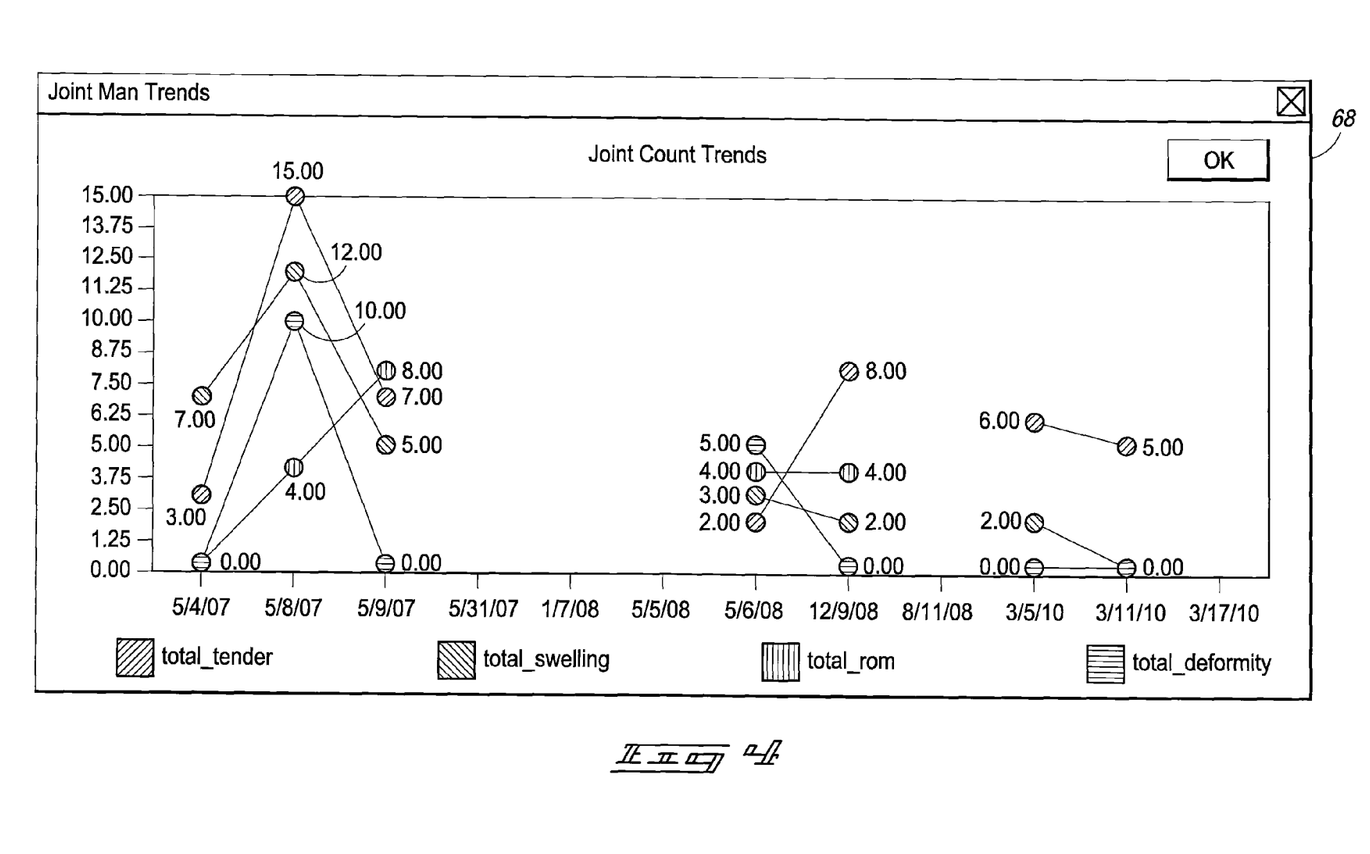
FIG. 4 is a graphical representation of trend data according to one embodiment.

In addition, the joint totals for the different conditions from the previous visit may also be retrieved from an appropriate database and also displayed. The % change of the current totals versus the previous totals may also be displayed to provide the medical personnel with a quick indication of whether the patient's disease has improved, degraded or remained substantially the same as the previous examination. The medical personnel may also select the "chart" button to generate a chart of trend information regarding the conditions of the joints. One example of the generated chart of trend data regarding the joints is shown in FIG. 4 and described below.

The graphical user interface 30 of FIG. 3 also includes a window 50 which may include information regarding an accepted outcome measure which may be used to describe the level of activity of the disease in the patient in a standardized way, for example, for comparison with other individuals and which may be used to analyze responses of the patient to previous treatments or drugs and to guide future treatment decisions in one implementation.

In accordance with the described example pertaining to rheumatoid arthritis, one example outcome measure is DAS28. Other outcome measures may be used in other embodiments. The indexed and standardized DAS28 outcome measure uses data from a plurality of parameters including conditions of tenderness (pain) and swelling of a plurality of 28 joints of the human body, laboratory information, and a physician's evaluation of the general health of the patient in terms of an amount of disease activity present in the patient resulting from the examination and observation of the patient. The pertinent joints for calculating the DAS28 score are the shoulders, elbows, wrists, metacarpophalangeal joints, proximal interphalangeal joints and the knees in the described embodiment.

In the depicted example of the graphical representation 32, data may be provided for joints in addition to the above-mentioned joints used for the DAS28 outcome measure. Accordingly, in one embodiment, the data (e.g., assigned conditions) of only some of the joints are used to determine a value of the outcome measure for the respective patient. The assigned conditions for the joints used for the DAS28 outcome measure may be used to determine the value for the outcome measure while the data regarding the other joints may be preserved in the patient's electronic record for completeness and additional information for use by the medical personnel with respect to additional joints of the patient.

The information for the parameters is combined to provide a value for the outcome measure which is indicative of the extent of the disease activity in the individual for the day of the examination. In the described example using the DAS28 outcome measure, the generated value may of the outcome measure may be referred to as a DAS28 score.

In one embodiment, the DAS28 score is calculated according to the following formula:

$$DAS28=0.56*\mathrm{sqrt}(tender28)+0.28*\mathrm{sqrt}(swollen28)+0.70*\ln(ESR)+0.014*GH$$

where swollen28 and tender28 are the number of swollen joints and tender joints, respectively, ESR is the Erythrocyte Sedimentation Rate in mm/hour and, GH is the patient's general health or global disease activity. The patient's general health may be measured on a visual analog scale (VAS) as determined by the physician in one embodiment.

In one embodiment, the graphical user interface 30 assists the medical personnel with generating the value of the outcome measure for the patient. More specifically, the medical personnel may select the "load JC data" button and the total numbers of swollen and tender joints as inputted by the medical personnel interfacing with the graphical representation 32 may be automatically imported into window 50. In other embodiments, the total numbers of swollen and tender joints may be automatically imported into window 50 following the indication of the joints which are swollen and tender by interaction with graphical representation 32.

The patient's ESR value may be entered by the medical personnel into window 50 if known. Alternatively, the "task lab" button may be selected to cause an automated task to be sent to an associated laboratory of the physician's office to provide the patient's ESR results.

The medical personnel may also input a general health value of the patient into window 50. Alternatively, the "VAS" button may be selected which provides a window shown in FIG. 5 and the physician may use the graphical interface thereof to input a value for the general health of the patient using a visual analog scale in one embodiment.

Following inputting of the information into window 50, the medical personnel may select the "calculate totals" button to generate the DAS28 score for the patient's current visit. In addition, the DAS28 score of the previous visit of the patient may also be retrieved from a database and displayed. Furthermore, a % change value of the current DAS28 score versus the DAS28 score of the previous visit may also be displayed to efficiently provide the medical personnel with comparison information regarding evaluation of the patient's disease over time.

The example graphical user interface 30 may also include a window 66 which provides a graphical indication of scores regarding the patient. In one example, the indicators may provide an efficient way of interpreting a patient's outcome measure. The example graphical indication illustrated in FIG. 3 may provide a quick reference or interpretation of the numerical value for the outcome measure. More specifically, in one embodiment, the window 66 includes three indicators which may be selected corresponding to the patient's current DAS28 score. A plurality of ranges of DAS28 scores may be used to select which indicator is displayed. In one example, a green indicator may be displayed in window 66 for a current DAS28 score of <2.6 and which indicates that the disease is currently in remission, an orange indicator may be displayed for a DAS28 score between 2.6-5 to indicate low-medium activity and a red indicator may be displayed for DAS28 scores which are >5.1 and which indicate a relatively high disease activity. The indicators of window 66 may be used as a quick guide providing information for the current disease activity of the patient in a graphical sense without the medical personnel having to readily recall numerical data ranges for interpretation of the numerical results of the outcome measures in one embodiment. Additional or alternative indicators may be used in other embodiments.

The graphical user interface 30 includes a window 52 for entering additional data. For rheumatoid arthritis, data for measures regarding a patient's physical function scores, such as health assessment questionnaire (HAQ) scores may be entered. In a more specific embodiment, a total activity score, a total tender/pain score, a total anxiety score, a general health score (from the patient's perspective) and an overall HAQ score may be calculated. For example, questions regarding the patient's ability to perform various activities may be used to calculate an activity score (e.g., whether the patient can dress themselves, whether the patient can get into or out of bed, lift a glass of water to their mouth, walk outdoors on flat ground, wash/dry their body, bend to pick up objects from the floor, turn faucets on/off, get into/out of a car, walk two miles, and/or participate in sports). Other pertinent questions include whether or not the patient had a good night's sleep, whether they can deal with feelings of anxiety of nervousness, whether the patient can deal with feelings of depression or feeling blue, and the patient's overall assessment of pain. The responses to the questions may be provided according to predetermined responses (e.g., without any difficulty, with some difficulty, with much difficulty, or unable to accomplish) which may be weighted and/or quantified and used to calculate numerical scores for activity, tender, anxiety, patient's general health and HAQ.

The graphical user interface 30 also includes a window 60 configured to display trend data regarding a history of values of an outcome measure (e.g., DAS28 scores) for the respective patient at a plurality of moments in time in the depicted example embodiment. Window 60 includes a graph including a plurality of markers corresponding to time along the x-axis and a scale of possible DAS28 score values along the y-axis. The DAS28 scores for the patient may be graphed versus different moments in time in the example window 60. Window 60 provides the medical personnel with a history of information regarding the DAS28 scores which may be quickly and efficiently reviewed and utilized for example to determine whether current treatment (e.g., medications) for the patient are appropriate or if modifications should be made to the patient's treatment.

As described in the example embodiment of FIG. 3, the graphical user interface 30 may assist the treating physician or other medical personnel with identifying the different conditions for the patient during the examination and provide a simple and efficient interface for inputting the conditions and other data regarding the patient into the computing system 10. The inputted information may be imported and further displayed in other alternative formats. For example, the data (e.g., list of joints and respective conditions) may be provided as raw data, graphically displayed in the graphical representation of the human anatomy, and included in a joint count table which includes a plurality of entries (e.g., different joints) and data pertinent to the patient for the entries (e.g., conditions of the joints of the patient) in some examples. The data may be used to calculate values of outcome measures described above to indicate the activity level of the disease in the patient, to determine whether the patient is responding to treatment, and/or which may also be used to determine appropriate courses of future treatment in some examples.

Graphical user interface 30 may also be used by the medical personnel to efficiently generate various reports regarding the patient's current examination and/or information regarding a plurality of examinations. The information inputted via the graphical user interface 30 may be used to generate additional reports for submissions to a medical agency 18 as described with respect to FIG. 6 and a chart note as described with respect to FIG. 7 in two illustrative examples.

The illustrated graphical user interface 30 includes a plurality of selectable boxes 68 which enable the medical personnel to specify the contents of subsequently generated reports. In the illustrated example, the medical personnel may select one or more of "joint count totals," "joint count table" and "DAS28" to have respective joint count total information from window 48, the joint count table from window 46 and outcome measure (e.g., DAS28) information from window 50 included in subsequently generated reports.

In one embodiment, graphical user interface 30 may also be used by the medical personnel to generate additional information and reports regarding patient information. In one example, the PQRI-RA link 70 may be selected which directs the medical personnel to another window, for example as discussed below with respect to FIG. 6, which assists the medical personnel with the generation of reports for submission to a medical agency 18, such as Medicare, for incentives for complying with quality measures of treatment and/or payment of the services for treatment.

The content of the graphical user interface 30 resulting from the patient visit may be stored as an electronic record for the patient, for example, within a database of the computing system 10. The electronic record may include the graphical representation 32 of the graphical user interface 30 shown in FIG. 3 with the pertinent data for the individual patient (e.g., respective joints displayed with the respective selected conditions). The stored information of the electronic record may additionally include all of the other displayed information of graphical user interface 30. The stored information may be used to generate different types of reports regarding the patient's health for various uses and which may also be stored as part of the electronic record of the patient using the database of the computing system 10.

For example, as discussed above, the inputted data may be used to generate a value of an outcome measure (e.g., DAS28 score) pertaining to the patient's health and which may be used by medical personnel for analysis of past treatment, for guidance in future treatment decisions and to describe activity of the disease of the patient. Trends of the patient's health may be provided to assist with determinations of whether the patient has responded favorably or not to certain medications and decisions for future treatment may be made using the recorded information in one embodiment. The information may be provided in a single comprehensive template (e.g., as shown in FIG. 3) in one embodiment, and the medical personnel may quickly review information regarding the inventory of joint conditions, past information, trend information, outcome measure information (e.g., DAS28 score) and HAQ information in the described example. The described examples of information which may be included are illustrative and the templates, reports and/or interfaces may be altered to accommodate additional and/or alternative information, for example pertaining to other medical specialties or treatments. Accordingly, the electronic report for a patient may include the graphical representation 32 of the anatomy with the different conditions indicated for the respective joints, associated tables, outcome measure data, reports, and trend data. The electronic reports may include any other data pertinent to the health of the patient.

Referring to FIG. 4, a window 68 is illustrated according to one embodiment which is displayed responsive to medical personnel selecting the "chart" button in window 48 of FIG. 3. The window 68 depicts trend information in the form of joint counts for the example application to arthritis treatment described herein. The joint information entered via graphical user interface 30 of FIG. 3 at different moments in time may be stored and graphed for efficient review of the patient's information over a period of time. In the illustrated example, the patient's information for total numbers of joints having the following different conditions are displayed: tender (painful), swelling, range of motion (ROM) decrease and deformity over a period of time from May 2007 to March 2010 in the illustrated example. The depicted example graph conveys information regarding the patient's health over a relatively significant period of time to the medical personnel in a straightforward and efficient manner.

Figure 5:
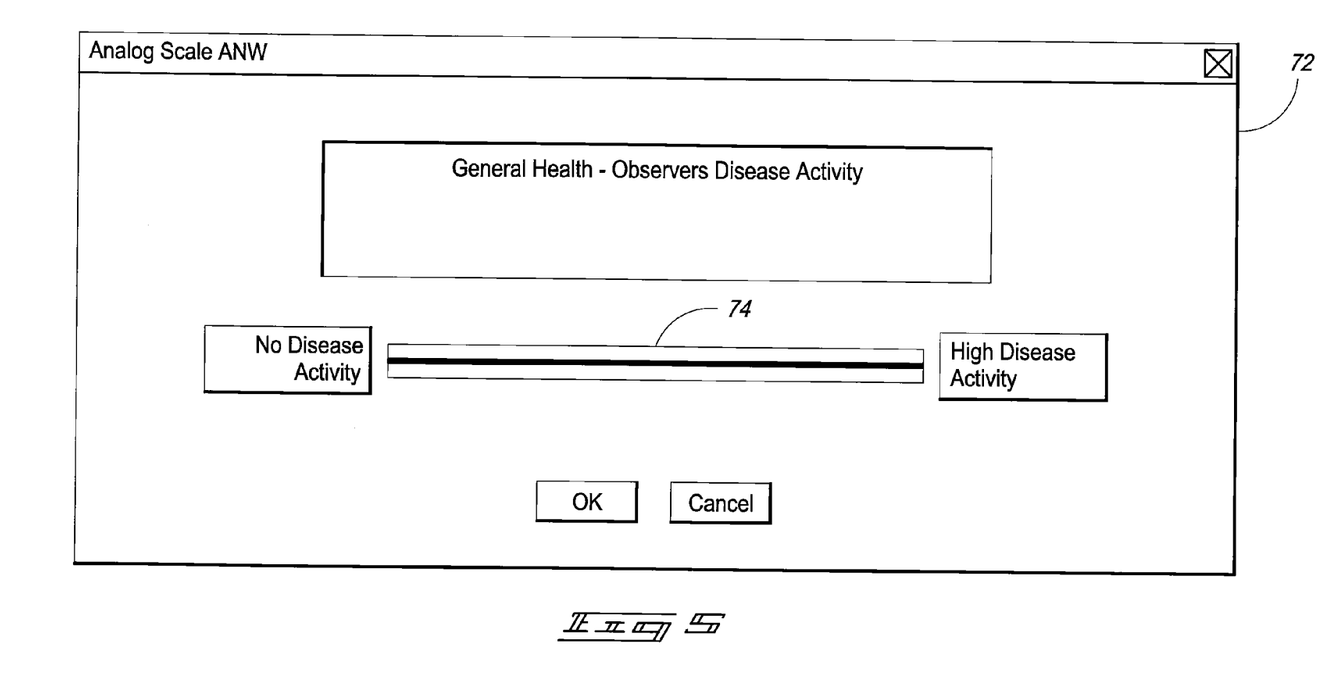
FIG. 5 is a graphical user interface which may be used by medical personnel to select a value of general health of a patient according to one embodiment.

Referring to FIG. 5, an example window 72 is displayed and which is generated responsive to a user selecting the VAS button of window 50 of graphical user interface 30 of FIG. 3. The illustrated window 72 assists the medical personnel with entering data regarding the patient's general health (GH) or global disease activity measured on a visual analog scale (VAS) in the depicted embodiment. The medical personnel may interact with a linear scale 74 of the window 72 to select a value for the general health of the patient based upon the examination. In the illustrated example, the scale extends from one extreme of "No Disease Activity" to another extreme of "High Disease Activity." A range of possible scores which may be selected are from 0 corresponding to "No Disease Activity" and extending to 10 corresponding to "High Disease Activity" in but one example. Once the medical personnel has selected an appropriate value on the linear scale 74, the user may press OK and the entered value will be imported into the window 50 of the graphical user interface 30 and used for DAS28 calculations in the described example. The entered data may also be stored for later retrieval. In other embodiments, the value of the general health may be entered in any appropriate method, for example by typing the score into the window 50.

Figures 6, 6A:
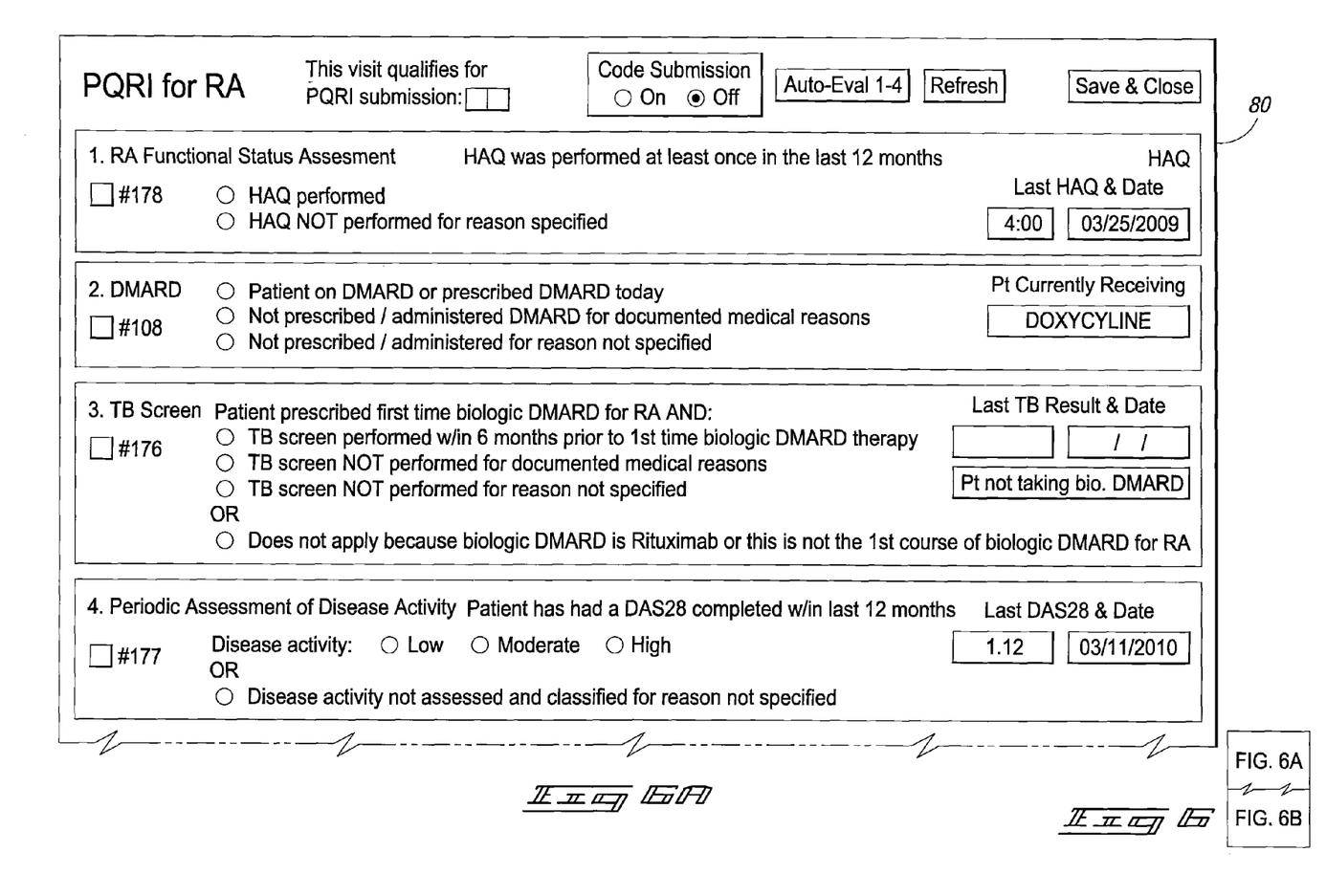
Figure 6B:
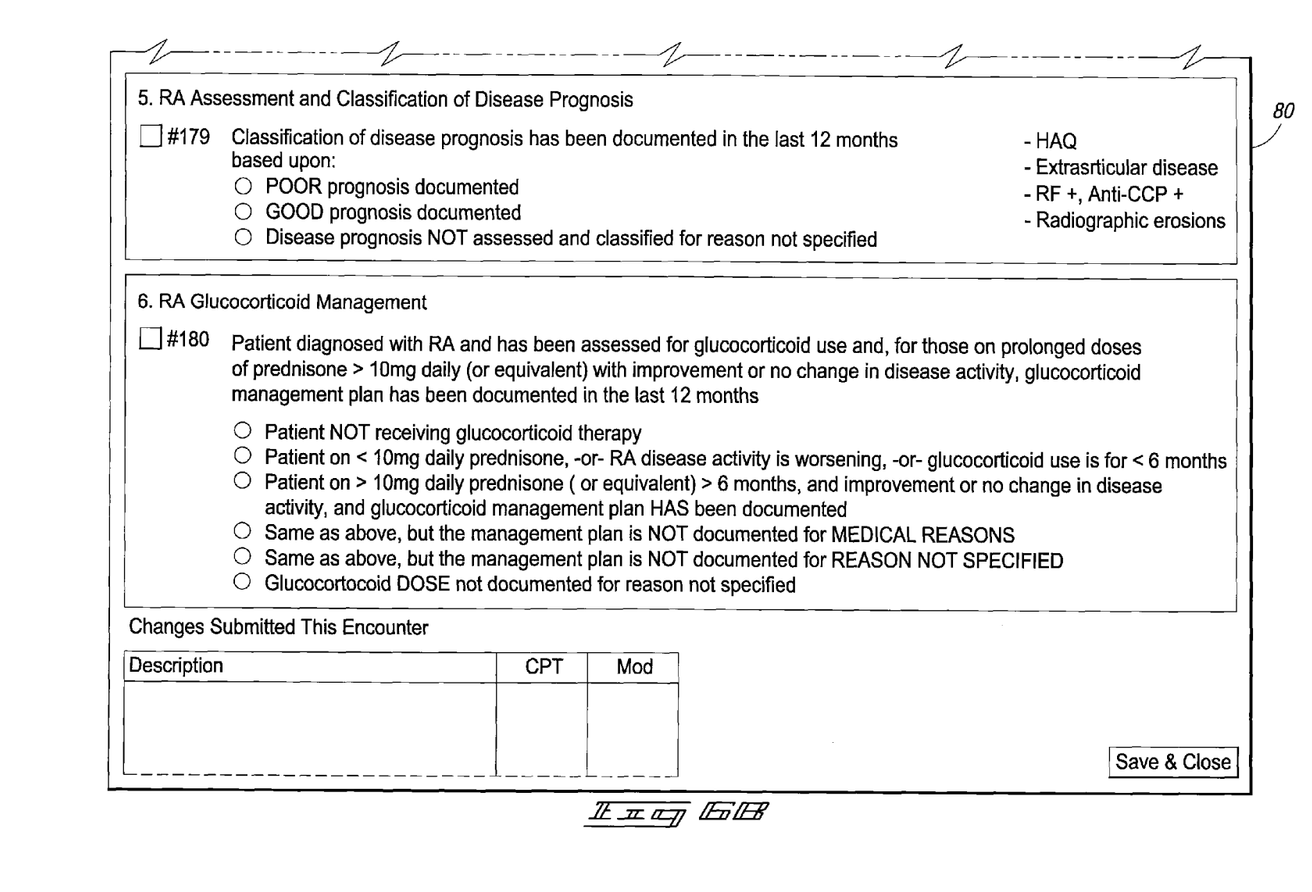

Referring to FIGS. 6A-6B, an example template 80 which may be displayed following selection of the PQRI-RA link 70 of the graphical user interface 30 is shown. The template 80 may be used to prepare submissions for qualifying with incentives and/or reimbursement for services from a medical agency 18, such as such a Medicare. In one specific example, the depicted template is for preparing Physician Quality Reporting Initiative-Rheumatoid Arthritis (PQRI-RA) submissions. Appropriate information regarding the patient's health already inputted into the computing system 10, for example the HAQ score and DAS28 score calculated via the graphical user interface 30 of FIG. 3, may be automatically imported from a database of computing system 10 into the template 80 without requiring manual entry by the medical personnel. Additional questions of the template 80 may be answered by medical personnel and the results may be saved. In one embodiment, the information of the completed template 80 may be reformatted into a submission for acceptance by the medical agency 18 and sent to the appropriate medical agency 18 (e.g., via a secured network connection) for incentives and/or reimbursement of costs and services incurred by the physician's office in treating the patient.

Figures 7, 7A:
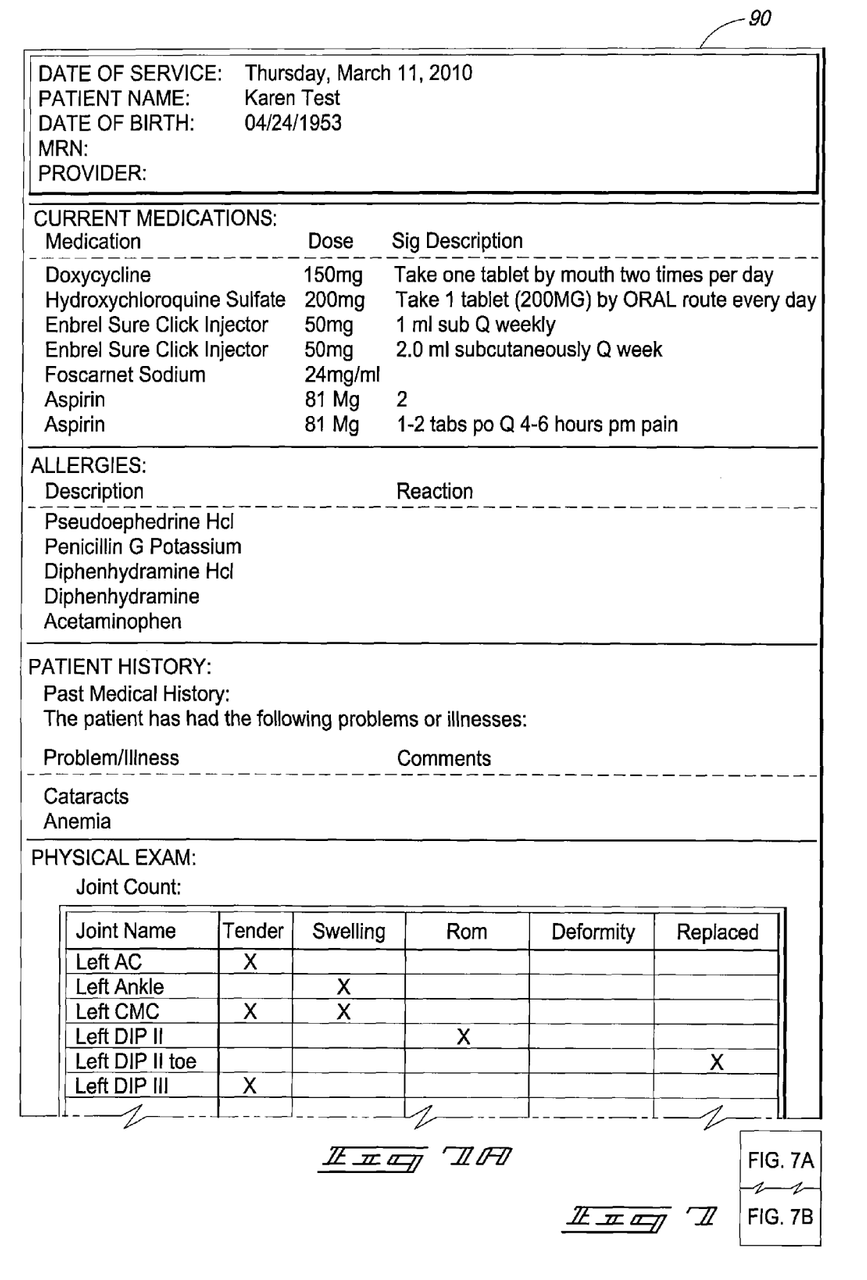

Referring to FIGS. 7A and 7B, an exemplary report regarding the patient's visit can be generated in the form of a chart note 90. During the examination, the medical personnel may input responses to a series of questions using their respective client device 12 and the responses may be displayed in the example chart note 90. The answers, such as medications, allergies, and other data regarding patient history may be provided on the chart note 90 as shown. Furthermore, the data results of the physical examination, for example the data of the joint count information of the table 46 of FIG. 3 entered via interaction with the human anatomy representation 32 or via other appropriate means can also be automatically imported into the chart note 90 from the database of the computing system 10 without manual entry by the medical personnel. The chart note 90 may be placed in the electronic medical record of the patient, printed for submission to other appropriate entities or physicians, and stored using the database of the computing system 10.

Figure 8:
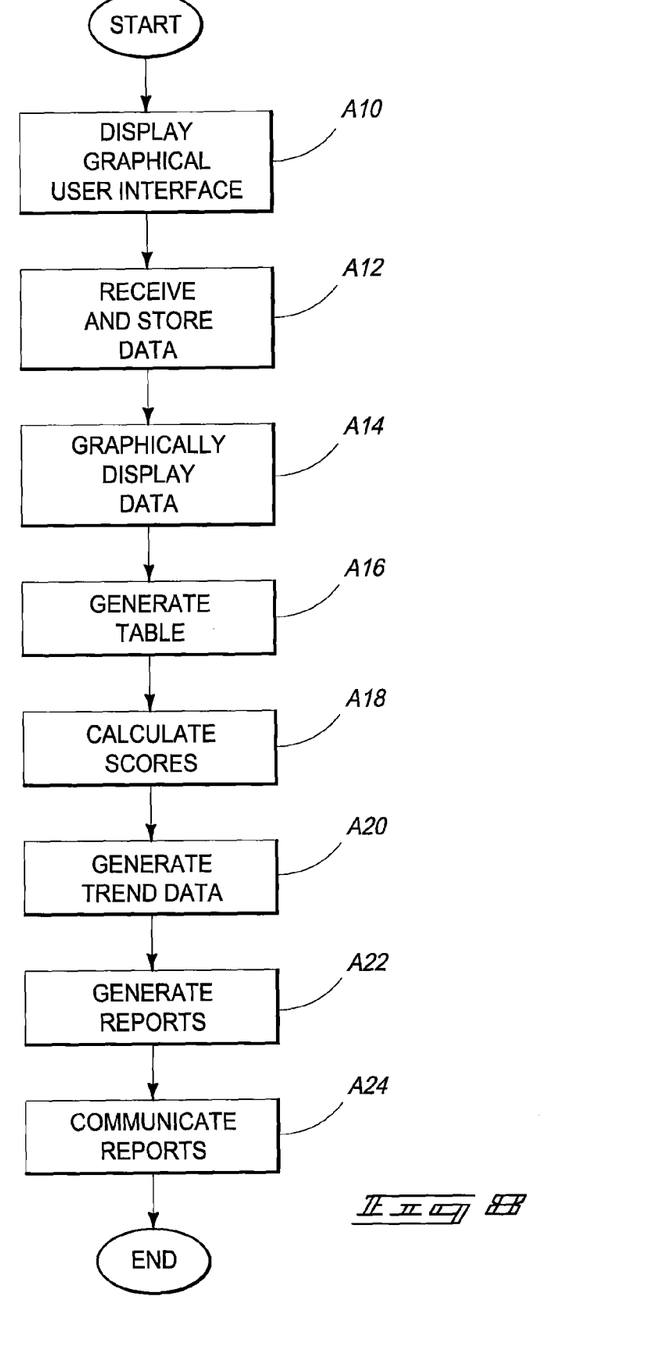
FIG. 8 is a flow chart illustrating an example method performed by the computing system according to one embodiment.
Figure 11B:
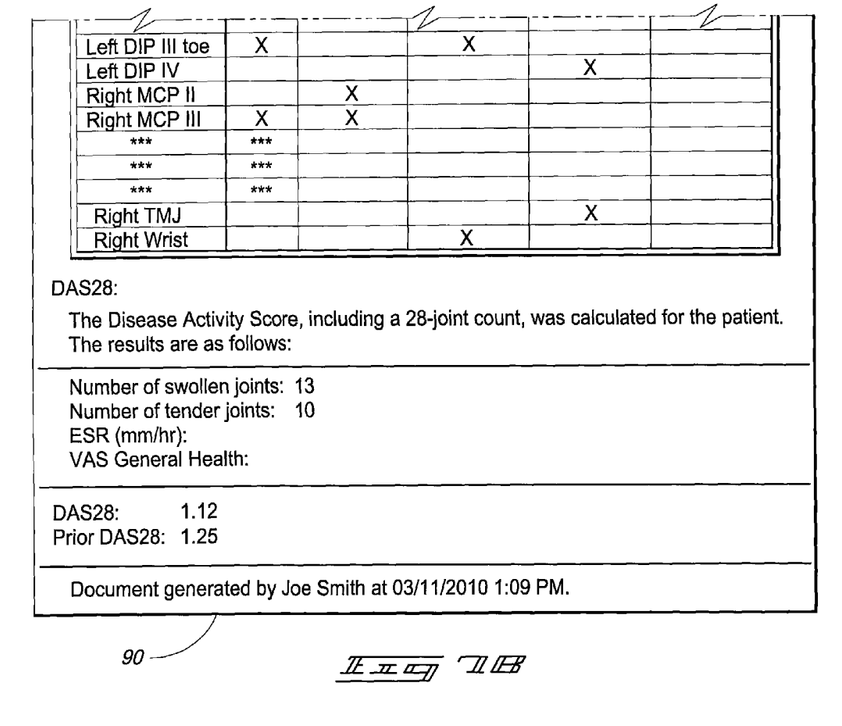

Referring to FIG. 8, a method which may be implemented by computing system 10 is shown according to one embodiment. Other methods are possible including more, less or alternative acts in other embodiments.

At an act A10, a graphical user interface may be displayed on a client device which includes a representation of the human anatomy in one embodiment.

At an act A12, an appropriate user may input information regarding a patient examination via the graphical user interface. For example, the inputted information regarding the patient's health may include a plurality of conditions for a plurality of joints of the patient in but one example pertaining to treatment of rheumatoid arthritis. The inputted data may be updated into an electronic record of the patient and stored. Previously-stored information and other data, such as laboratory data, may be accessed at act A12 and perhaps combined with the newly entered data.

At an act A14, the graphical user interface may graphically represent the information regarding the patient's health. For example, different colors may be associated with different joints to indicate the different conditions of the patient's joints at the time of the examination.

At an act A16, one or more table of the information regarding the patient's health may be generated (and perhaps displayed using the graphical user interface).

At an act A18, scores or values, for example, for an outcome measure for the patient may be calculated using the information regarding the patient's health (and perhaps displayed using the graphical user interface).

At an act A20, the information for the current visit may also be combined with other stored data to provide trend data, for example joint count trends, DAS28 trends, etc. (and perhaps displayed using the graphical user interface).

At an act A22, appropriate reports may be generated using the information pertaining to the patient's health (and perhaps displayed using the graphical user interface). For example, chart notes, submissions to other entities or any other desired reports including the information pertinent to the health of the patient may be generated and displayed.

At an act A24, the generated reports containing the information pertinent to the patient's health may be stored and communicated to appropriate recipients (e.g., medical agency 18, referring physicians, etc.).

Although aspects of the present disclosure may be utilized to record information regarding patients having various diseases or conditions, some of the aspects of the disclosure are discussed above with respect to rheumatoid arthritis. Compiled information regarding different conditions of different joints of the body is helpful in determining the extent of the disease in a patient being treated as well as ascertaining the patient's response to different treatments over time and may be a useful tool for formulating future treatments.

Rheumatoid arthritis is one of the most frequent potentially crippling joint diseases followed by rheumatologists-arthritis specialists. Fortunately, there have been relatively recent major changes in the therapeutic approaches as well as therapeutic options available for treatment of rheumatoid arthritis which have provided improved results for treating rheumatoid arthritis. For example, the increasing use of immunosuppressive agents (methotrexate, leflunomide, azathioprine) and subsequent development of biotech medications (TNF inhibitors, Orencia, Rituxan) have clearly changed the rates of progressive joint damage, deformity, and functional capacity and increased the life expectancy of patients who have rheumatoid arthritis.

However, these medications have significant toxicity, and the bioactive medications are extremely expensive drugs. Even in the best outcome trials, a high-grade response to any medication is seen in less than approximately 50% of patients. Accordingly, major issues in treatment remain of how to best follow patients and make decisions about when they are doing well or poorly and at what point changes in drug therapies between the available agents should be made.

As discussed above, various information may be used by medical personnel to treat patients. Physician visual analog scales (VAS) of estimated active joint inflammation, laboratory measurements of inflammation (ESR) and measures of patient's physical function scores (health assessment questionnaire-HAQ scores) are used to attempt to detect changes in joint inflammation/disease activity over time. The pooling of this information is important since all of these factors are valuable in follow-up of groups of patients. Furthermore, the provision of this information may be important for treatment of individual patients who may have isolated features that are indicative of their disease evolution. At least some aspects of the disclosure enable efficient recordation, generation and maintenance of the information for efficient recollection, compilation, use and review by medical personnel.

More recently, the above-described composite outcome measure scoring system DAS28 has been utilized which combines mathematically weighted variables discussed above including swollen and tender joint scores, general health estimates of disease activity by the physician, and laboratory measure of inflammation (ESR). At least some aspects of the disclosure described above enable treating physicians to efficiently input information pertinent to the composite outcome measure scoring system and the computing system 10 may automatically calculate the outcome measure scores and provide different representations of the scores and associated data, for example, by graphing and including trend information of scores over time.

DAS28 scores have been shown to correlate well with medication responses in trials and this measurement system is increasingly used in clinical trials worldwide and clinics have been gradually adopting daily use of these measurements in outpatient settings in an attempt to attach numerical scores to disease activity and use of these scores to "drive" changes in therapy. The described example DAS28 scoring system is useful for detecting change in joint inflammation and at least some aspects of the disclosure facilitate analysis of DAS28 scores and tracking of disease activity over time, for example by providing trend data of DAS28 scores indicative of a patient's activity over time. At least some aspects of the disclosure provide improvements of recording and providing trend data regarding plural examinations of a patient compared with typical day-to-day clinical examinations where joint examinations are performed but clinicians rarely go back over time to see if there are significant progressive changes in various parameters being monitored.

At least some aspects of the disclosure facilitate electronic capture of information regarding swollen and tender joints that indicate joint disease activity and potential for progressive joint damage, along with data regarding joints that are becoming more restricted or deformed. This electronic information may be easily provided into understandable tables and graphs and other representations for use by medical personnel and which may also be easily stored and tracked over time. The ability to quickly and easily record information regarding joint tenderness, swelling, deformity and range of loss enable presentation of the information in different formats and templates which is extremely helpful in a real-life clinical situations and enables medical personnel to easily assess current disease activity and recent progression in joint damage/function as well as identify more subtle changes which can be tracked over time. By the end of a clinical exam, a clinician can immediately assess information regarding progression of active or deforming/limiting joint disease.

As mentioned above, current medications used to slow or stop progression of rheumatoid arthritis have significant toxicity and increasingly very high cost. Accordingly, it is important to use these medications in the best possible way for patient care and also to quickly recognize if expensive and somewhat risky drug therapies are not providing sufficient benefit and should be stopped. It is believed that the ease of inputting, recording and reporting of patient's information provided by aspects of the present disclosure provide an efficient tool for use by medical personnel to treat diseases, including rheumatoid arthritis. It is believed that aspects of the present disclosure which facilitate the recording of patient's information and the efficient provision of the information into one or more desired format are of increased importance in the era of "evidence based medicine" where both patients and insurers want both the best and most cost efficient management of disease. The generated reports can be used to determine whether patients are responding favorably to treatment (e.g., medicates) or whether the treatment should be changed. The reports may be used to justify costs for treatment in some examples by efficiently providing data in a format which indicates the patient's responses to treatment.

It is believed that the disclosed example aspects of capturing, generating and recording electronic data can allow the real life clinician to have easy and time efficient access to information which is vital for treatment of disease. Although aspects of the disclosure are described with respect to rheumatoid arthritis, the disclosed aspects are applicable to treatment of other diseases and other health conditions, especially chronic diseases with relatively long-term poor outcomes where tracking of a mix of clinical, laboratory and patient functional data can allow more optimal medical decision making. At least some aspects of the disclosure bring measurement parameters laboriously used in clinical trials to a level that can be efficiently applied to daily clinical patient management and treatment in one embodiment.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

Further, aspects herein have been presented for guidance in construction and/or operation of illustrative embodiments of the disclosure. Applicant(s) hereof consider these described illustrative embodiments to also include, disclose and describe further inventive aspects in addition to those explicitly disclosed. For example, the additional inventive aspects may include less, more and/or alternative features than those described in the illustrative embodiments. In more specific examples, Applicants consider the disclosure to include, disclose and describe methods which include less, more and/or alternative steps than those methods explicitly disclosed as well as apparatus which includes less, more and/or alternative structure than the explicitly disclosed structure.

What is claimed is:

1. A computer-implemented medical information recording method comprising:
    displaying a graphical user interface including a graphical representation of a plurality of joints of a human anatomy;
    accessing user inputs interacting with the graphical representation of the joints of the human anatomy, the user inputs comprising data pertaining to a health of a patient including associations of different conditions with different ones of the joints; and
    generating an electronic record which includes the data pertaining to the health of the patient including the associations of the different conditions with the different ones of the joints.

2. The method of claim 1 wherein the user inputs select the different ones of the joints.

3. The method of claim 1 wherein the generating comprises generating the electronic record including a table having a plurality of entries corresponding to the joints and including the associations of the different conditions with the different ones of the joints.

4. The method of claim 1 wherein the generating comprises generating the electronic record in the form of an outcome measure which is indicative of a level of disease in the patient.

5. The method of claim 1 wherein the accessing comprises accessing the user inputs which result from interactions of medical personnel with the patient at one moment in time, and wherein the generating comprises generating the electronic record including the data comprising trend data pertaining to the health of the patient at a plurality of moments in time including the one moment in time.

6. The method of claim 5 further comprising generating a graph of the trend data pertaining to the health of the patient at the plurality of moments in time including the one moment in time.

7. The method of claim 1 wherein the displaying comprises displaying the graphical user interface comprising the data pertaining to the health of the patient.

8. The method of claim 1 further comprising:
    selecting some of the data pertaining to the health of the patient which corresponds to an outcome measure which is indicative of disease activity in the patient; and
    calculating a score for the outcome measure using the some of the data pertaining to the health of the patient.

9. The method of claim 8 wherein the calculating comprises calculating the score using a plurality of parameters, and further comprising displaying a visual analog scale for one of the parameters, and accessing user input interacting with the visual analog scale which selects a value for the one of the parameters used in the calculation of the score of the outcome measure.

10. The method of claim 8 further comprising accessing laboratory information regarding the individual, and wherein the calculating comprises calculating the score using the laboratory information.

11. The method of claim 8 wherein the selecting comprises selecting the conditions for some of the joints.

12. The method of claim 8 wherein the user inputs result from interactions of medical personnel with the patient at one moment in time, and the generating comprises generating the electronic record comprising trend data regarding the patient comprising a plurality of scores of the outcome measure at a plurality of moments in time including the one moment in time.

13. The method of claim 1 further comprising generating a report comprising the data pertaining to the health of the patient for submission to a medical agency with respect to compensation for services of medical personnel treating the patient.

14. The method of claim 1 wherein the generating comprises generating the electronic record comprising a table including a plurality of entries for the different ones of the joints, and the data including the conditions associated with the different ones of the joints.

15. The method of claim 1 wherein one of the conditions is associated with a plurality of the joints, and further comprising determining a total number of the joints having the one of the conditions.

16. The method of claim 1 further comprising determining total numbers of the joints having the respective different conditions.

17. A computer configured to generate medical information for a patient comprising:
a display device configured to display a graphical user interface including a graphical representation of a plurality of joints of a human anatomy; and
processing circuitry configured to:
access user inputs interacting with the graphical representation of the joints of the human anatomy, the user inputs comprising data pertaining to a health of a patient including associations of different conditions with different ones of the joints; and
generate an electronic record which includes the data pertaining to the health of the patient including the associations of the different conditions with the different ones of the joints.

18. The computer of claim 17 wherein the processing circuitry is configured to use the joints with the associated conditions to determine a value of an outcome measure which is indicative of a level of activity of arthritis in the patient and to generate a report including the value of the outcome measure and a table having a plurality of entries corresponding to the joints of the human anatomy and the different conditions associated with different ones of the joints.

19. The computer of claim 18 wherein the processing circuitry is configured to determine the value of the outcome measure using laboratory information and a value indicative of the general health of the patient.

20. The computer of claim 17 wherein the processing circuitry is configured to access the user inputs which result from interactions of medical personnel with the patient at one moment in time, and to generate trend data pertaining to the health of the patient at a plurality of moments in time including the one moment in time.

21. At least one computer-readable storage media comprising programming configured to cause processing circuitry to perform processing comprising:
displaying a graphical user interface including a graphical representation of a plurality of joints of a human anatomy;
accessing user inputs interacting with the graphical representation of the joints of the human anatomy, the user inputs comprising data pertaining to a health of a patient including associations of different conditions with different ones of the joints; and
generating an electronic record which includes the data pertaining to the health of the patient including the associations of the different conditions with the different ones of the joints.

22. The at least one computer-readable storage media of claim 21 further comprising programming configured to cause processing circuitry to perform processing comprising determining a value of an outcome measure using the different conditions associated with the different ones of the joints of the patient.

23. The at least one computer-readable storage media of claim 21 wherein the displaying comprises displaying a table having a plurality of entries corresponding to the joints of the human anatomy and the different conditions associated with the different ones of the joints.

24. The at least one computer-readable storage media of claim 21 wherein the displaying comprises displaying the graphical representation of the human anatomy which graphically indicates the different conditions associated with the different ones of the joints.

* * * * *

UNITED STATES PATENT AND TRADEMARK OFFICE
CERTIFICATE OF CORRECTION

PATENT NO. : 8,458,610 B2
APPLICATION NO. : 12/726281
DATED : June 4, 2013
INVENTOR(S) : Howard M. Kenney et al.

It is certified that error appears in the above-identified patent and that said Letters Patent is hereby corrected as shown below:

In the Specification

Column 3, line 6 – Replace "examples Client" with --examples. Client--

Column 10, line 48 – Replace "such as such a Medicare." with --such as Medicare.--

Column 13, lines 12-13 – Replace "clinical situations" with --clinical situation--

Column 13, line 32 – Replace "desired format are" with --desired formats are--

Signed and Sealed this
Thirteenth Day of August, 2013

Teresa Stanek Rea
*Acting Director of the United States Patent and Trademark Office*